(12) United States Patent
Jamison (10) Patent No.: US 7,721,612 B2
(45) Date of Patent: May 25, 2010

(54) REAL-TIME FILTRATION APPARATUS AND ASSOCIATED METHODS

(75) Inventor: Dale E. Jamison, Humble, TX (US)

(73) Assignee: Halliburton Energy Services, Inc., Duncan, OK (US)

( * ) Notice: Subject to any disclaimer, the term of this patent is extended or adjusted under 35 U.S.C. 154(b) by 340 days.

(21) Appl. No.: 12/041,056

(22) Filed: Mar. 3, 2008

(65) Prior Publication Data

US 2009/0217776 A1 Sep. 3, 2009

(51) Int. Cl.
*G01N 1/22* (2006.01)
(52) U.S. Cl. .................................................. 73/863.23
(58) Field of Classification Search ............. 73/152.22, 73/61.63, 61.64, 863.23
See application file for complete search history.

(56) References Cited

U.S. PATENT DOCUMENTS

| | | | | |
|---|---|---|---|---|
| 3,010,583 A | * | 11/1961 | Kenyon | 210/406 |
| 3,172,286 A | * | 3/1965 | Cave et al. | 73/61.64 |
| 4,397,177 A | | 8/1983 | Cain | 73/61.63 |
| 5,052,219 A | | 10/1991 | Fery et al. | 73/152.22 |
| 5,105,656 A | | 4/1992 | Jackson | 73/61.63 |
| 6,543,276 B2 | | 4/2003 | Murphy, Jr. et al. | 73/61.4 |

OTHER PUBLICATIONS

International Search Report and Written Opinion from PCT/GB2009/000519, dated Jul. 29, 2009.

* cited by examiner

*Primary Examiner*—Hezron Williams
*Assistant Examiner*—Tamiko D Bellamy
(74) *Attorney, Agent, or Firm*—John W. Wustenberg; Baker Botts, LLP (57) ABSTRACT

A fluid testing apparatus and associated method include a testing chamber, a filter storage device and a filter transfer mechanism. The testing chamber has a sample volume, a filtrate collection reservoir, an opening between the sample volume and the filtrate collection reservoir, and at least one port into the sample volume. The filter transfer mechanism positions at least one filter in the opening. The opening is closed and a sample fluid, introduced into the port, at least partially fills the sample volume. The sample volume is pressurized and a filtrate of the sample fluid flows from the sample volume, through the filter into the filtrate collection reservoir. The volume of filtrate passing into the filtrate collection reservoir is measured and the sample fluid from sample volume is discharged. The filtrate is discharged from the filtrate collection reservoir, and the filter transfer mechanism removes the filter.

20 Claims, 13 Drawing Sheets

REAL-TIME FILTRATION APPARATUS AND ASSOCIATED METHODS

BACKGROUND

The present disclosure, according to specific example embodiments, generally relates to improved methods for characterizing the performance of fluids. In particular, the present disclosure relates to a high temperature, high-pressure fluid filtration test apparatus, and associated methods of use.

In drilling wells for production of hydrocarbons from underground formations, drilling mud typically cycles through a well bore during drilling. In addition to driving a drill motor and cleaning a drilling bit, the drilling mud also provides a column of fluid that exerts pressure on the formation pierced by the well bore, which prevents or reduces fluid from a reservoir or formation from entering the well bore. In addition, drilling mud may infiltrate the formation in the region surrounding the well bore (the near well bore region).

A problem often encountered during subterranean treatments is the undesired loss or leak off of fluid into the formation. This undesired loss or leak off is commonly referred to as "fluid loss." Such treatments include, but are not limited to, drilling operations, cleanup operations, workover operations, completion operations, stimulation treatments (e.g., fracturing, acidizing), and sand control treatments (e.g., gravel packing). In fracturing treatments, fluid loss into the formation may result in a reduction in fluid efficiency, such that fracturing fluid cannot propagate the fracture as desired.

Fluid loss into the formation may result from a number of downhole conditions, such as high-formation permeability, overbalance pressures, perforated or open-hole intervals in the well bore, and large differential pressures associated with differential segregation in wells completed in a multilayer reservoir. In some instances, the fluid loss may be into a low-pressure portion of the formation due to overbalance pressures, for example, where a well is completed in a multilayer reservoir.

Traditional methods of characterizing the performance of fluids have involved a high pressure, high temperature filtration test. High Pressure, High Temperature (HPHT) filtration tests are used to measure filtration behavior of water or oil based drilling fluids at elevated temperatures, usually according to the specifications of the American Petroleum Institute (API). These tests are typically time intensive due to their setup requirements, testing protocol, and clean-up operations. As drilling rig time, space on offshore rigs, and personnel become more expensive, there exists a need for a method of testing fluids that requires less manpower and time.

SUMMARY

The present disclosure, according to specific example embodiments, generally relates to improved methods for characterizing the performance of fluids. In particular, the present disclosure relates to an automated high temperature, high pressure fluid filtration test device and associated methods of use.

In accordance with one method of the present invention, a fluid testing method comprises providing a fluid testing apparatus. The fluid testing apparatus includes a testing chamber with a sample volume, a filtrate collection reservoir, an opening between the sample volume and the filtrate collection reservoir, and at least one port into the sample volume. The fluid testing apparatus further includes a filter storage device and a filter transfer mechanism. The method further comprises positioning at least one filter in the opening using the filter transfer mechanism, closing the opening, introducing a sample fluid into the port to at least partially fill the sample volume, pressurizing the sample volume, allowing a filtrate of the sample fluid to flow from the sample volume, through the filter and into the filtrate collection reservoir, measuring the volume of filtrate passing into the filtrate collection reservoir, discharging sample fluid from the sample volume, discharging filtrate from the filtrate collection reservoir, and removing the filter.

In accordance with one apparatus of the present invention, a fluid testing apparatus comprises a testing chamber. The testing chamber includes a sample volume and a filtrate collection reservoir, with an opening therebetween, a filtrate volume detector, and at least one port. The fluid testing apparatus further comprises a filter storage device and a filter transfer mechanism.

In accordance with one system of the present invention, a fluid testing system comprises a fluid testing apparatus. The fluid testing apparatus includes a testing chamber. The testing chamber has a sample volume and a filtrate collection reservoir, with an opening therebetween, a filtrate volume detector, and at least one port. The fluid testing apparatus also includes a filter storage device, a filter transfer mechanism, at least one filter positioned between the sample volume and the filtrate collection reservoir, and a sample fluid in the testing chamber.

The features and advantages of the present invention will be readily apparent to those skilled in the art. While numerous changes may be made by those skilled in the art, such changes are within the spirit of the invention.

BRIEF DESCRIPTION OF THE DRAWINGS

These drawings illustrate certain aspects of some of the embodiments of the present invention, and should not be used to limit or define the invention.

DESCRIPTION OF PREFERRED EMBODIMENTS

The present disclosure, according to specific example embodiments, generally relates to improved methods for characterizing the performance of fluids. In particular, the present disclosure relates to a high temperature, high pressure fluid testing apparatus and associated methods of use.

The apparatus and methods of the present disclosure allow for improvements to traditional high temperature, high pressure filtration tests. These traditional tests have been performed both in the laboratory environment as well as at the rig site. The methods and apparatus of the present disclosure may allow for trend analysis of drilling fluids in real time. Methods currently used in the art for the analysis of drilling fluids are time consuming, and typically provide results only after a job has been performed. Real-time analysis using the apparatus and methods of the present disclosure would allow for monitoring and adjustment of the fluid properties of a drilling fluid during a job such that the properties of the drilling fluid may be adjusted accordingly to obtain desired fluid characteristics. For example, the temperature and pressure may be monitored.

Current methods of testing drilling fluids require a skilled operator to manage and perform the tests. Moreover, the quality of testing results may be affected by operator technique and attentiveness. The apparatus and methods of the present disclosure may allow for greater consistency and quality of fluid testing results and eliminate the need for an operator, thereby reducing costs associated with performing a job. Moreover, the methods and apparatus of the present disclosure may allow for faster, more reliable fluid testing results than those results obtained using methods currently known in the art.

The fluid testing apparatus of the present disclosure may be useful in real-time testing of properties of fluids intended for use in subterranean formations. The properties of the fluid that may be tested, include, but are not limited to, the volume of filtrate collected from the fluid, filter cake formation on a filter, and emulsion properties. The testing apparatus of the present disclosure may be used on location at a rig site. Advantageously, the fluid characteristics, as determined by testing, may be adjusted accordingly during a job to obtain optimal fluid characteristics in anticipation of problems encountered during subterranean operations. The conventional HTHP filtration test is run at 600 psi on the sample and 100 psi on the filtrate (providing a 500 psi pressure drop across the filter), and 300° F., for 30 minutes. Depending on whether one is following the API "Recommended Practice for Field Testing of Oil-based Drilling Fluids" (API Practice 13B-2 Mar. 2005), or the API "Recommended Practice for Laboratory Testing of Drilling Fluids" (API Practice 13I February 2004), total filtrate volume may be read at 30 minutes and reported, or multiple reading of filtrate volume may be taken during the 30 minute test. Due to the crude nature of the conventional apparatus in terms of filtrate collection, temperature control, and manual pressure setting, a multi-variable test is not run, i.e. the test is run at single sample pressure, pressure drop and temperature for the duration of filtrate collection. In reality, the drill mud must perform at a variety of well depths which produce a wide range of pressures and temperatures. Therefore, knowledge of mud plugging properties as a function of absolute pressure, pressure drop, and temperature may permit the engineer to better optimize the mud for a particular well, and knowledge of how these properties of a mud change with time may permit improved corrections to the mud chemistry during drilling.

The apparatus of the present invention may allow readings of filtrate volume to be taken at any desired frequency, e.g. every second. This may provide the ability to ramp or hold the temperature of the vessel as desired, and can change sample pressure and filtrate pressure independently, thereby changing not only the pressure drop across the filter but the absolute pressure as well, all the while taking filtrate volume or filtrate flow rate measurements. This capability may allow for a multi-variable statistical test program to determine the coefficients in a mathematical model that describes the plugging characteristics of the mud, all in a single, computer controlled test run. For example, in a single pressure/pressure-drop/temperature test, like the conventional HTHP manual tests, the data may match the filtrate volume versus square root of time response predicted by cake filtration theory. Performing a multi-variable test may provide information about the compressibility of the sample and filtrate fluids as well as properties of the filtrate cake such as compressibility or cake porosity, resistance to fluid flow, changes with absolute pressure, pressure drop and temperature.

In certain embodiments, during drilling operations, the apparatus of the present disclosure may be used as a quality control test for drilling fluids. Drilling fluid may be circulated into the subterranean formation. When the drilling fluid, returns to the surface, the apparatus of the present disclosure may be used to test for fluid properties of the circulated fluid. In certain embodiments, the fluid may be tested prior to circulation. In certain other embodiments, the fluid may be tested prior to, during, and following circulation into the subterranean formation. In certain embodiments, following testing of the fluid using an apparatus of the present disclosure, the fluid may be recirculated into the subterranean formation. Prior to recirculation, the properties of the fluid may be adjusted to optimize the fluid characteristics for a particular downhole environment so as to minimize the amount of fluid loss into the formation during subterranean operations. The testing may be repeated as desired by one of ordinary skill in the art so that fluid characteristics are optimized throughout the drilling procedure.

To facilitate a better understanding of the present invention, the following examples of certain embodiments are given. In no way should the following examples be read to limit, or define, the scope of the invention.

Figure 1:
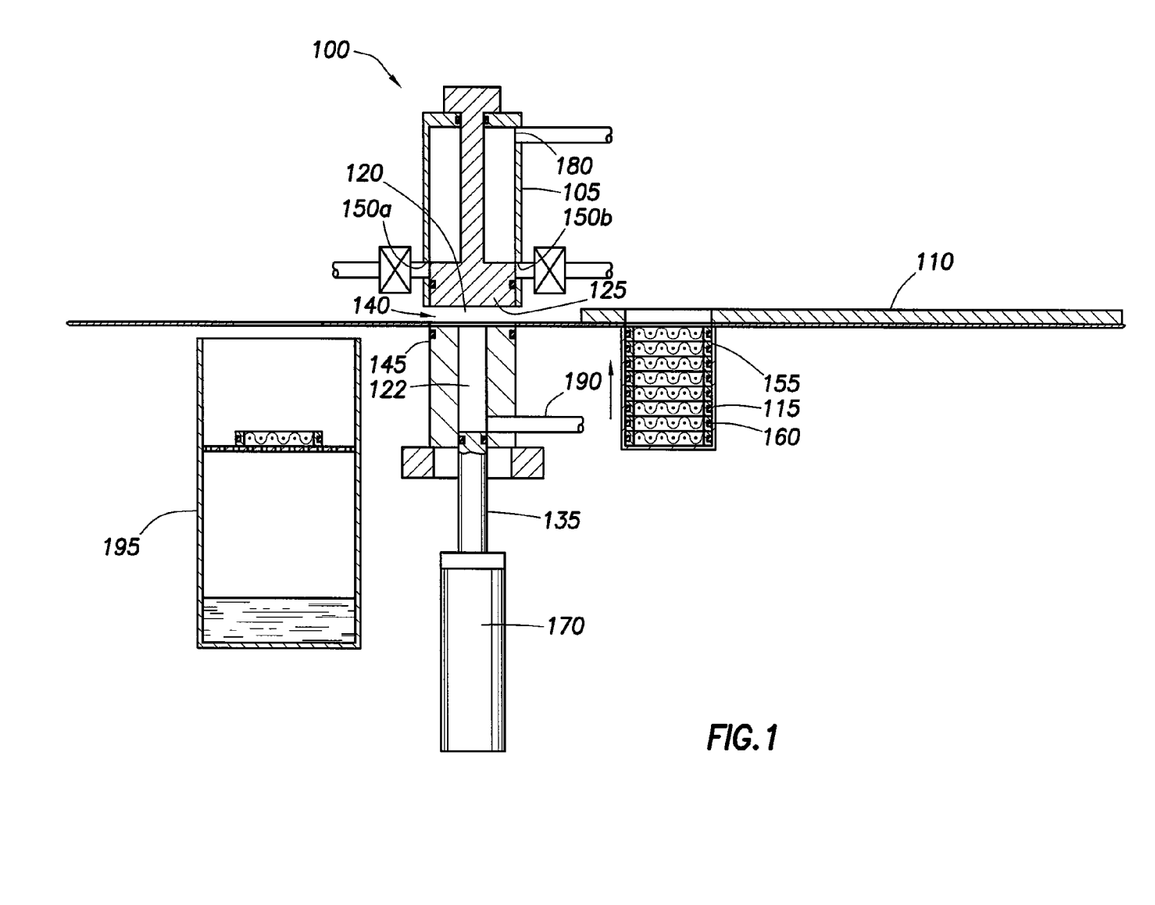
FIG. 1 illustrates a cross-sectional view of a fluid testing apparatus, according to one embodiment of the present disclosure.

FIG. 1 illustrates a cross-sectional view of fluid testing apparatus 100, according to one embodiment of the present disclosure. Fluid testing apparatus 100 generally includes testing chamber 105, filter transfer mechanism 110, and filter storage device 115.

Testing chamber 105 includes sample volume 120 and filtrate collection reservoir 122. Although depicted as distinct portions within testing chamber 105, sample volume 120 and filtrate collection reservoir 122 may each be separate chambers of testing chamber 105. A floating piston 125 or a fluid pressurization piston may be positioned within sample volume 120 to prevent gas from reacting with sample fluid 130. Alternatively, gas pressure alone may be used to pressurize sample volume 120, without the presence of floating piston 125. In yet other embodiments, a mechanical force may be applied to floating piston 125, as by a motorized ball screw or a hydraulic or pneumatic cylinder, without the introduction of any gas into testing chamber 105.

Filtrate volume detector 135 may be a piston positioned within filtrate collection reservoir 122. Alternatively, filtrate volume detector 135 may be a sensor or other device positioned within filtrate collection reservoir 122 or outside filtrate collection reservoir 122. An opening 140 may be provided between sample volume 120 and filtrate collection reservoir 122. In certain embodiments, opening 140 may be selectively closed using filtrate support 145. Testing chamber 105 may also have at least one port 150.

Testing chamber 105 may be any chamber with suitable geometry that can accommodate any pistons, test fluid, filter, and sealing requirements and that is capable of maintaining desired temperature and pressure ranges for testing fluids of interest. For example, testing chamber 105 may be capable of withstanding and maintaining testing temperatures up to about 450° F. and testing pressure differentials of about 500 pounds per square inch. In various embodiments, temperatures may be between 200° F. and 500° F., and in some instances about 300° F. Fluids that may be tested using fluid testing apparatus 100 may be any treatment fluid used in a subterranean formation. Such treatment fluids include, but are not limited to, drilling fluids, invert emulsions, oil-based fluids, water based fluids, and fracturing fluids.

Figure 2:
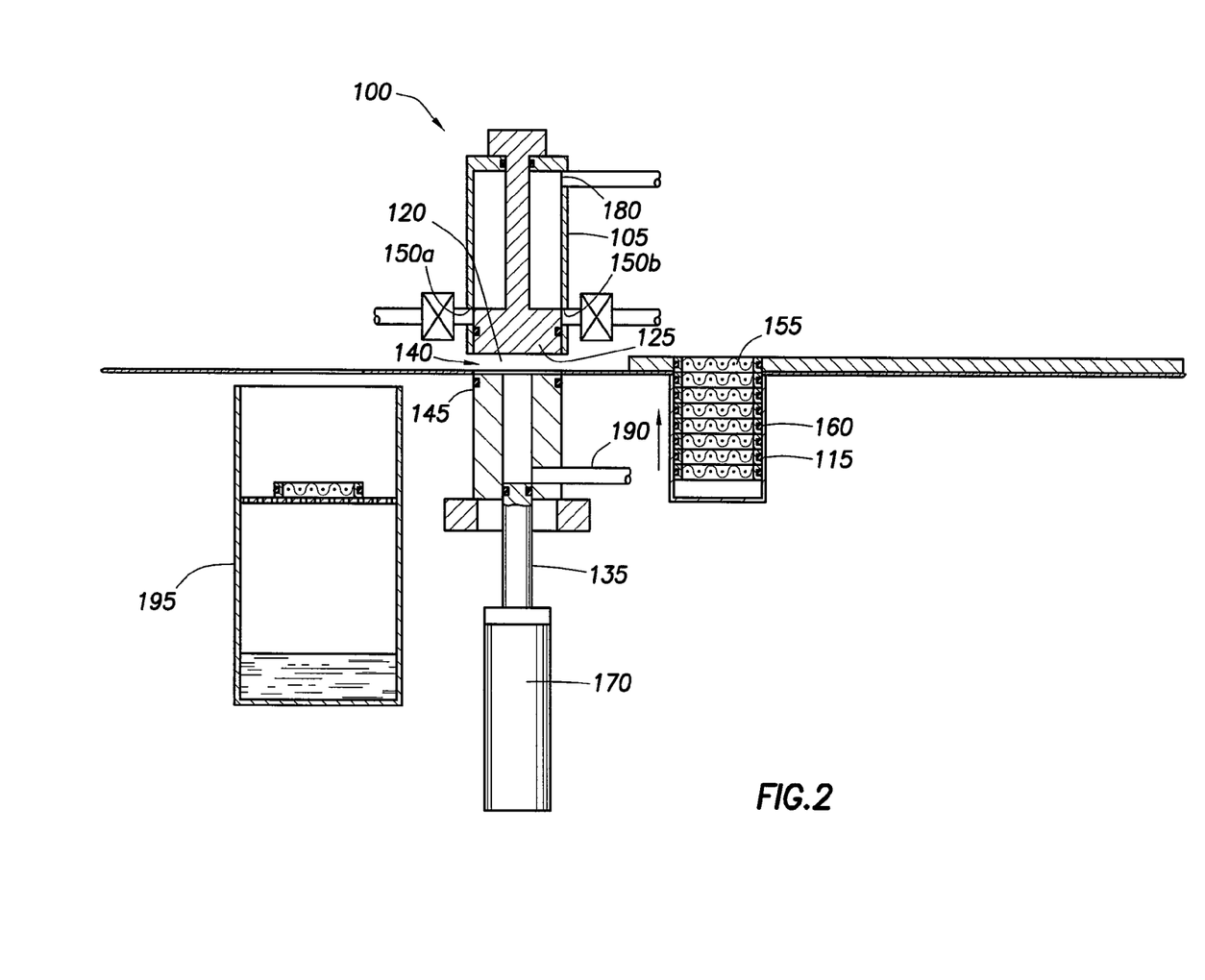
FIG. 2 illustrates a cross-sectional view of the fluid testing apparatus of FIG. 1, showing a filter moving into a filter transfer mechanism.
Figure 3:
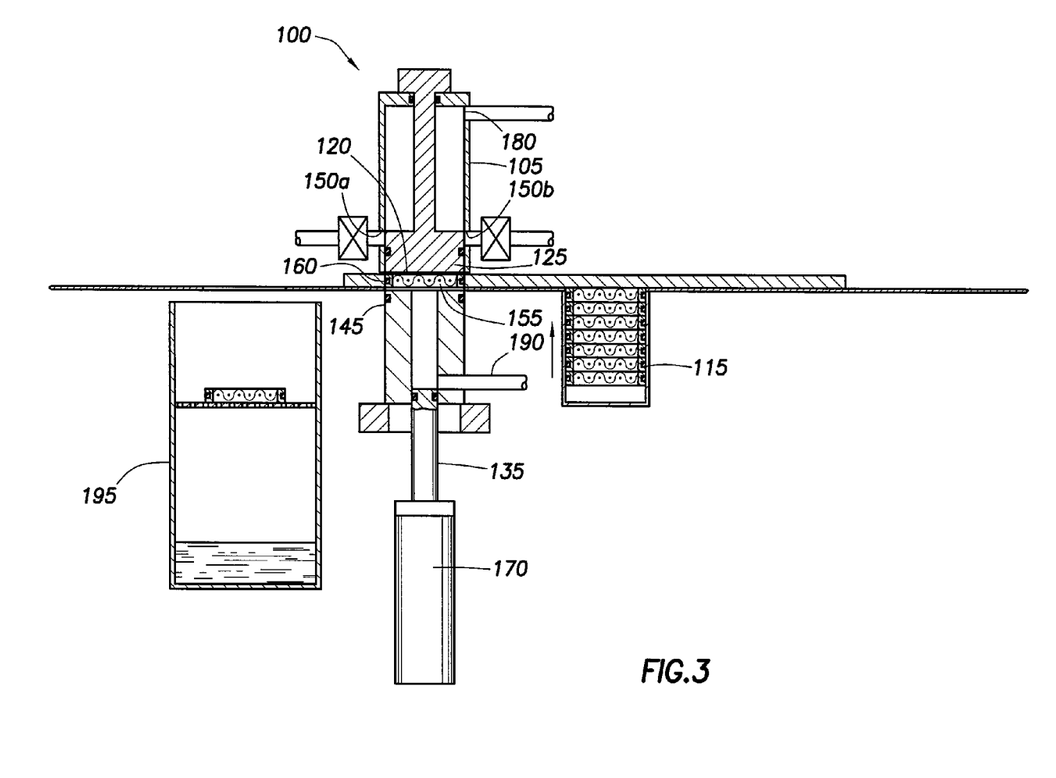
FIG. 3 illustrates a cross-sectional view of the fluid testing apparatus of FIGS. 1 and 2, showing the filter positioned between a sample volume and a filtrate collection reservoir.

Referring now to FIG. 2, a single filter 155 may be moved from filter storage device 115, which may be a chamber holding a stack of similar filters. As illustrated, the top filter 155 of filter storage device 115 moves into filter transfer mechanism 110. Filter transfer mechanism 110 may be a shuttle mechanism, capable of moving a filter from filter storage device 115, to testing chamber 105, and to disposal area 195. In certain embodiments, filter transfer mechanism 110 may employ a car to position and move filter 155. As shown in FIG. 3, filter transfer mechanism 110 may move filter 155 and position it opening 140 between sample volume 120 and filtrate collection reservoir 122. Filter 155 may be, for example, a synthetic ceramic disk (e.g., 30 or 60 to 100 micron) with one or more seals 160. The pore size of filter 155 may vary depending upon the particular fluid to be tested and testing conditions. While a single filter 155 is shown, slight modification could be made to allow for multiple filters to be used simultaneously. Filter 155 may be any of a number of different types of filters and is not limited to ceramic disks. For example, filter 155 may be a portion of a roll of continuous filter media.

Figure 13:
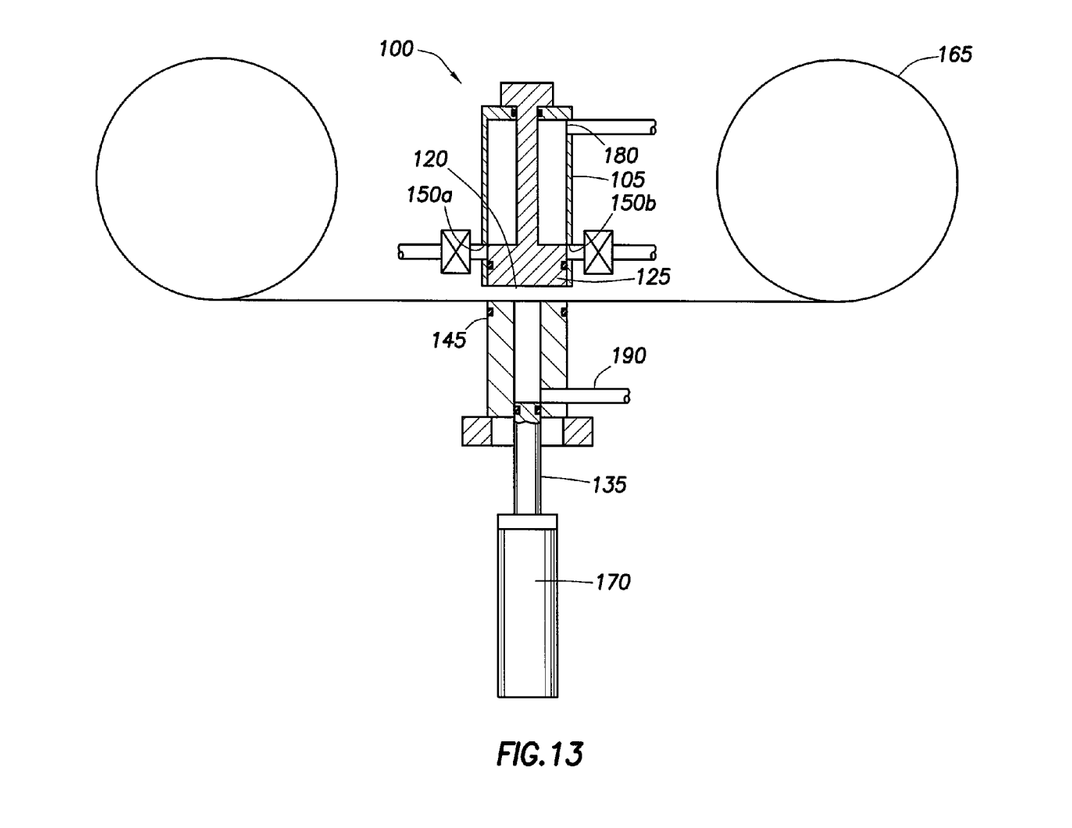
FIG. 13 illustrates a cross-sectional view of a fluid testing apparatus, according to another embodiment of the present disclosure.

Filter storage device 115 may be any means by which multiple filters may be stored prior to use during testing. In certain embodiment, filter storage device 115 may be a chamber comprising a stack of filters. In an alternative embodiment illustrated in FIG. 13, filter storage device 115 may be at least one reel of continuous filter media 165. Filter transfer mechanism 110 may be any mechanism by which filter 155 may be transported from filter storage device 115 and positioned between sample volume 120 and filtrate collection reservoir 122. For example, in certain embodiments, a shuttle mechanism employing a car may be used to move filter 155 from filter storage device 115 to opening 140. Filter transfer mechanism 110 may also be capable of removing filter 155 from opening 140 for disposal after testing.

Figure 4:
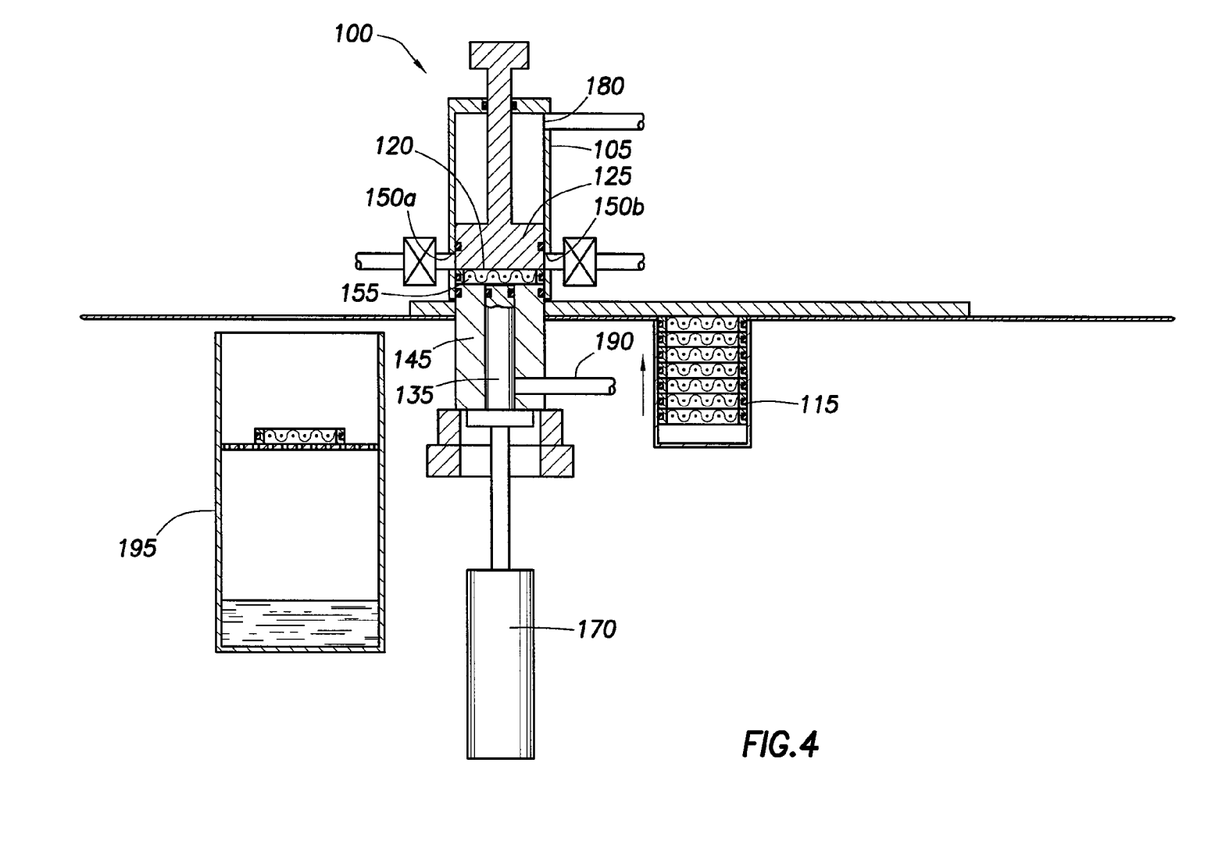
FIG. 4 illustrates a cross-sectional view of the fluid testing apparatus of FIGS. 1-3, showing the filter after being moved upward into the sample volume.

Referring now to FIG. 4, following placement of filter 155 in opening 140, filtrate loader 170 and/or filtrate support 145 may manipulate the position of filter 155. For example, filter 155 may be moved upward into sample volume 120. Filtrate loader 170 may move filtrate support 145 upward, causing filter 155 to move into sample volume 120. This may cause opening 140 to be closed, with seals 160 creating isolation of testing chamber 105. Seals 160 may be dynamic seals, such as quad o-ring type seals.

Figure 5:
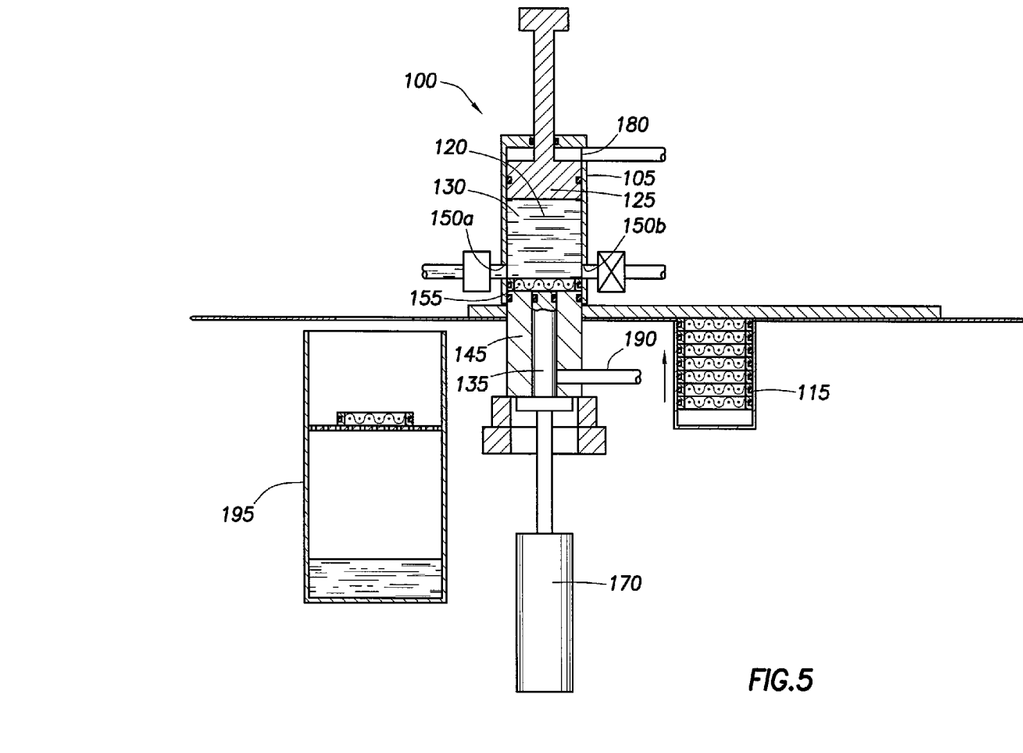
FIG. 5 illustrates a cross-sectional view of the fluid testing apparatus of FIGS. 1-4, showing a sample fluid in the sample volume.
Figure 6:
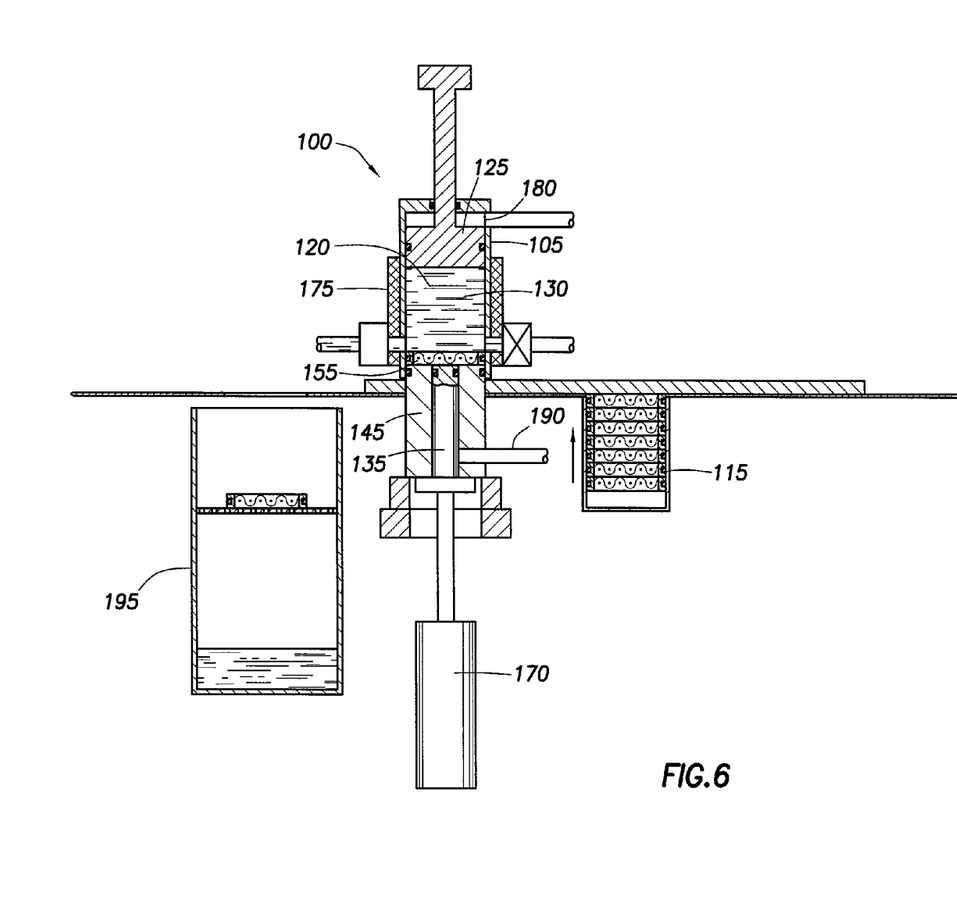
FIG. 6 illustrates a cross-sectional view of the fluid testing apparatus of FIGS. 1-5, showing a heater.

Referring now to FIGS. 5 and 6, port 150a of testing chamber 105 allows for sample fluid 130 to enter testing chamber 105 to at least partially fill sample volume 120, as illustrated in FIG. 5. As sample volume 120 fills, floating piston 125 may move upward. Once a desired testing volume of sample fluid 130 is present in sample volume 120, port 150a is closed, as shown in FIG. 6. Heater 175 may be used to apply heat to sample fluid 130, so as to replicate "downhole" conditions. Heater 175 may be used to heat the entire testing chamber 105 and may be, for example, an electrical resistance band heater attached to an exterior of testing chamber 105. While heater 175 is shown only in FIGS. 6 and 7, heater 175 may be present throughout and turned on only when heating is desired.

Figure 7:
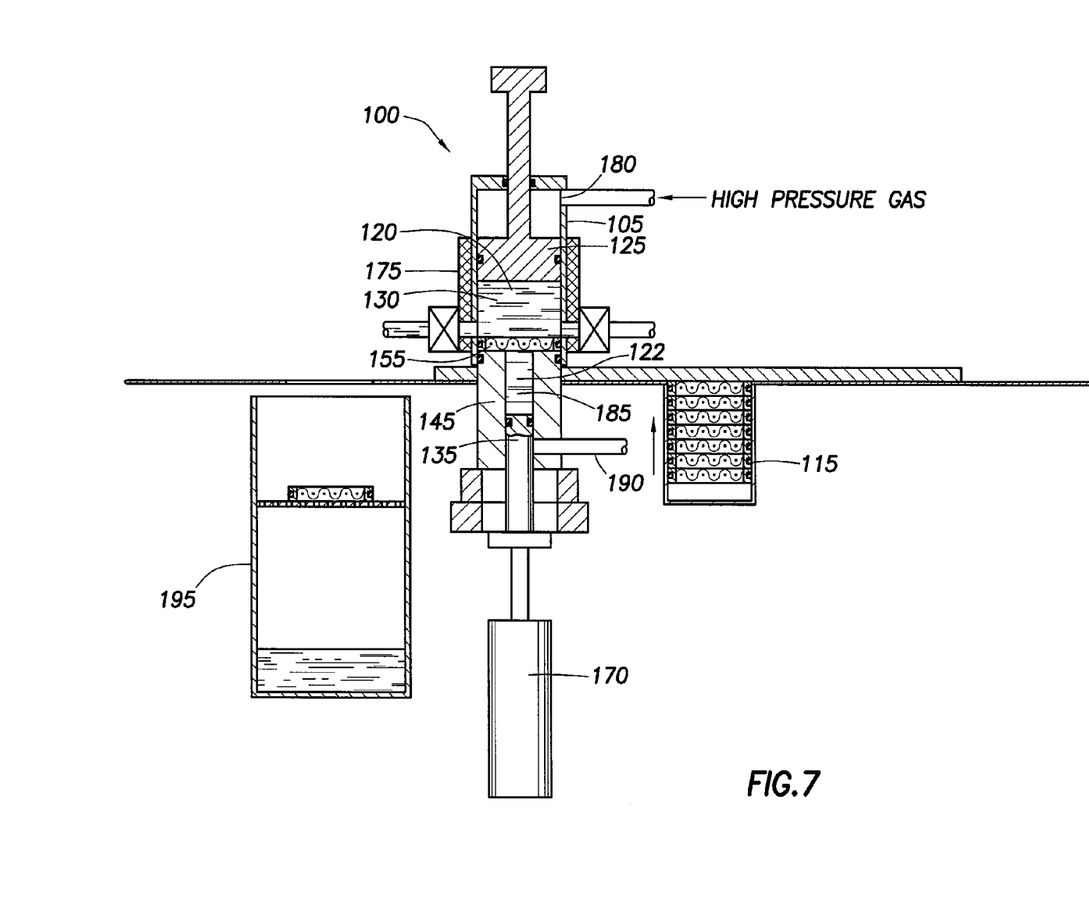
FIG. 7 illustrates a cross-sectional view of the fluid testing apparatus of FIGS. 1-6, showing filtrate in the filtrate collection chamber.

Referring now to FIG. 7, pressure may be introduced via gas input 180. This may allow floating piston 125 to compress heated sample fluid 130, further replicating "downhole" conditions. Port 180 allows high pressure gas to maintain the desired pressure on sample fluid 130 to effect filtration during the test or to prevent boiling of sample fluid 130 during heat-up and cool-down portions of the cycle. Alternatively, sample fluid 130 may be pressurized and/or heated prior to placement in testing chamber 105.

Filtrate loader 170 may be adjusted so that differential pressure across sample fluid 130 may be maintained at a desired set point. This may be done, for example, by applying a pressurized gas, as from a bottle of compressed gas and a pressure regulator, to filtrate collection reservoir 122.

An alternate way to both apply a controlled pressure to filtrate 185 and measure a volume of filtrate 185 is to use a piston as filtrate volume detector 135. Filtrate volume detector 135 may measure a volume of filtrate 185 passing through filter 155 and into filtrate collection reservoir 122. A force may be applied to the piston by an external means to achieve a desired filtrate pressure and the position of the piston can be measured to determine the quantity of filtrate 185 produced over time, as by a linearly variable differential transformer.

As filtrate 185 passes through filter 155, the piston may be displaced downward in filtrate collection reservoir 122 so as to maintain a particular differential pressure across sample fluid 130 at a desired set point. Typically, the desired differential pressure set point is in the range of about 100 to about 500 psi. Filtrate 185 may be collected in filtrate collection reservoir 122 during the testing period. As the volume of filtrate 185 increases, the piston displaces further within filtrate collection reservoir 122.

The external force on the piston may be applied by filtrate loader 170, which may be a pneumatic cylinder controlled by a computer. Filtrate loader 170 may be the prime mover to open and close testing chamber 105 during replacement of filter 155. Filtrate loader 170 may actuate filtrate support 145, which may also be a cylinder. Filtrate support 145 may have one or more seals 160 to effectively close testing chamber 105 and may lock to maintain closure during testing.

Filtrate loader 170, among other things, may prevent any boiling of filtrate 185 in testing chamber 105. The volume of filtrate 185 may be collected over the testing period and recorded in real time. In certain embodiments, for example when the volume of filtrate 185 is measured by the displacement of a piston, a computer may be used to monitor and/or record the displacement. Thus, data pertaining to the volume of filtrate measured may be accumulated in real time. By accumulating data in real time, properties of non-sample fluid associated with sample fluid 130 may be adjusted immediately at the rig site to fit a particular job. Moreover, this data may be made available to other rig operators in the region of the job site as well as in other areas of the world. This continuous or near-continuous measurement of filtrate properties may allow a final result to be predicted sooner, thus reducing testing time. For example, data may be taken continuously (e.g. once per second) for several minutes and extrapolated to predict final filtrate volume achieved in 30 or 60 minutes without running the test for that duration. Once the ultimate reading has been obtained, the test may conclude and a new test may begin.

Figure 8:
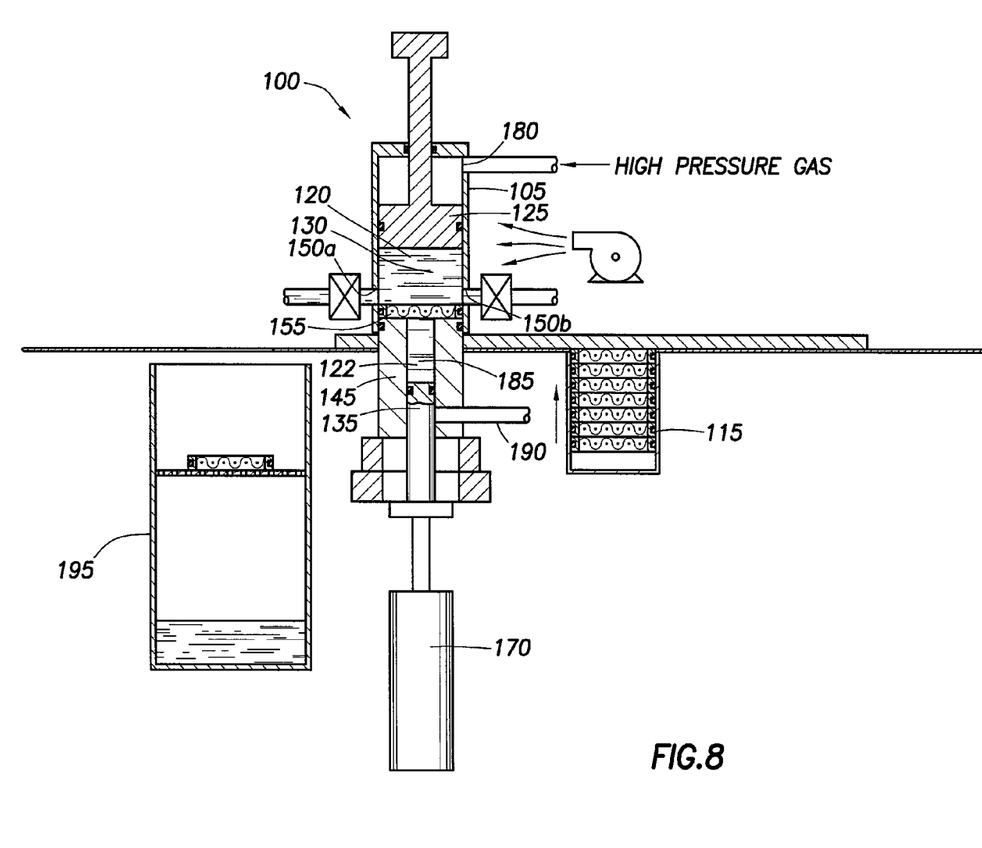
FIG. 8 illustrates a cross-sectional view of the fluid testing apparatus of FIGS. 1-7, showing cooling.
Figure 9:
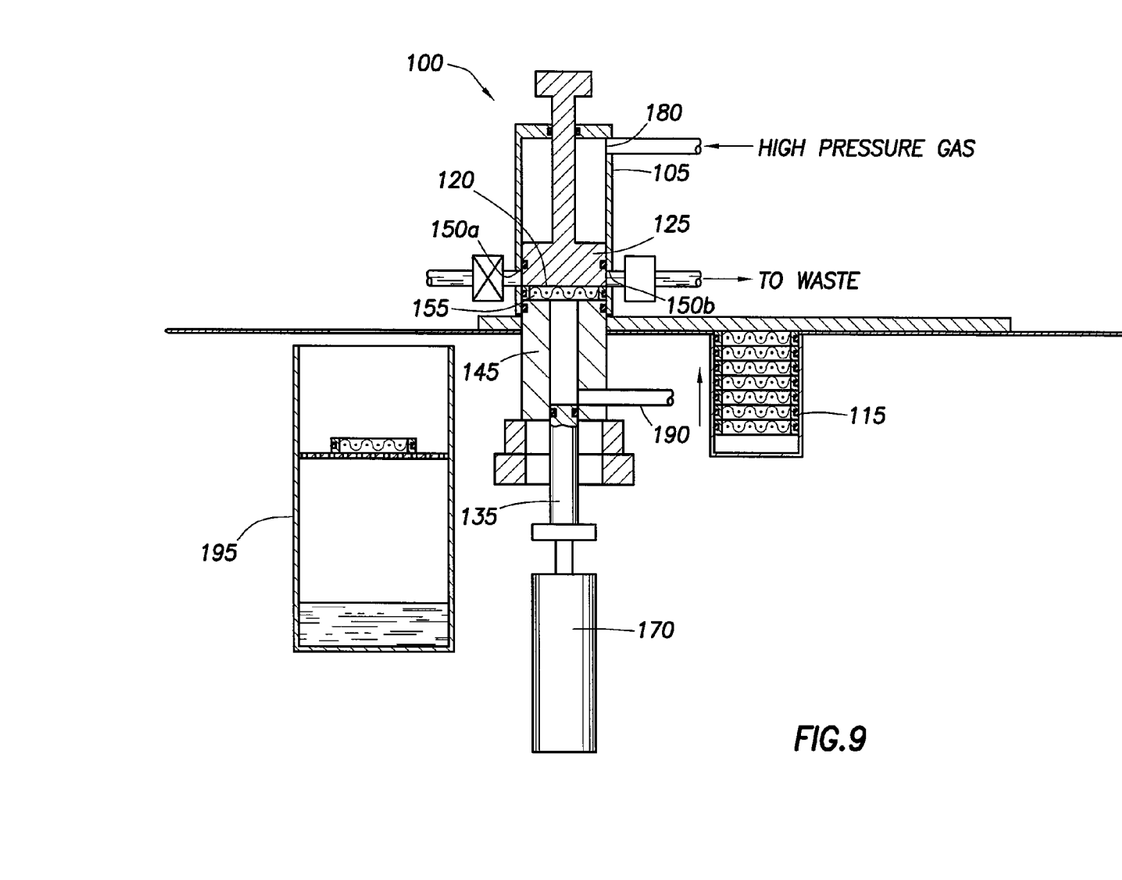
FIG. 9 illustrates a cross-sectional view of the fluid testing apparatus of FIGS. 1-8, showing discharge of fluid from the apparatus.

Referring now to FIG. 8, following testing, clean-up operations may commence. Cooling may be achieved by circulating cool air over the exterior of fluid testing apparatus 100. For example, cool air may pass over heater 175, providing cooling, which may prevent any flash to steam. Referring now to FIG. 9, fluid sample 130 may be discharged by opening valve 150*b* and providing pressure via 180 to force floating piston 125 downward. Floating piston 125 may also serve to clean sample volume 120. Filtrate loader 170 may be retracted, allowing filtrate 185 to discharge out of filtrate collection reservoir 122 through drain 190.

A flush fluid (not shown), typically the same base oil or water as the sample to be tested, may be introduced via 150a after discharging the spent test sample to help remove the remnants of the test sample and reduce the cross contamination between consecutive samples. In addition, such flush fluid may be introduced into fluid collection reservoir 120 at the start of the test cycle, after inserting a new filter. This flush fluid can then be forced thru the new filter to displace any entrained air within the filter to improve initial filtrate accuracy, and then excess flush fluid can be exhausted through 150*b* by manipulation of floating piston 125 and filtrate volume detector 135 just prior to introducing the test sample.

Figure 10:
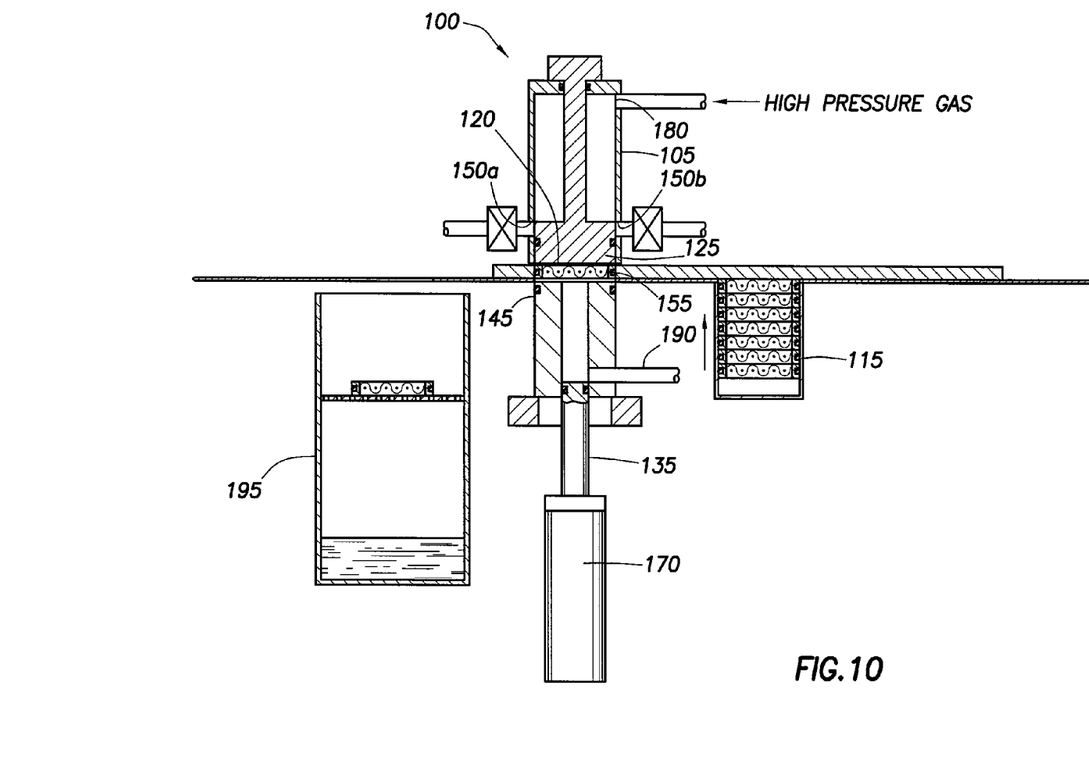
FIG. 10 illustrates a cross-sectional view of the fluid testing apparatus of FIGS. 1-9, showing the filter moved back into filter transfer mechanism.

Referring now to FIG. 10, Floating piston 125 may be lowered to contact filter 155 and push it downward, along with filtrate support 145, to a position such that filter 155 may be removed.

Figure 11:
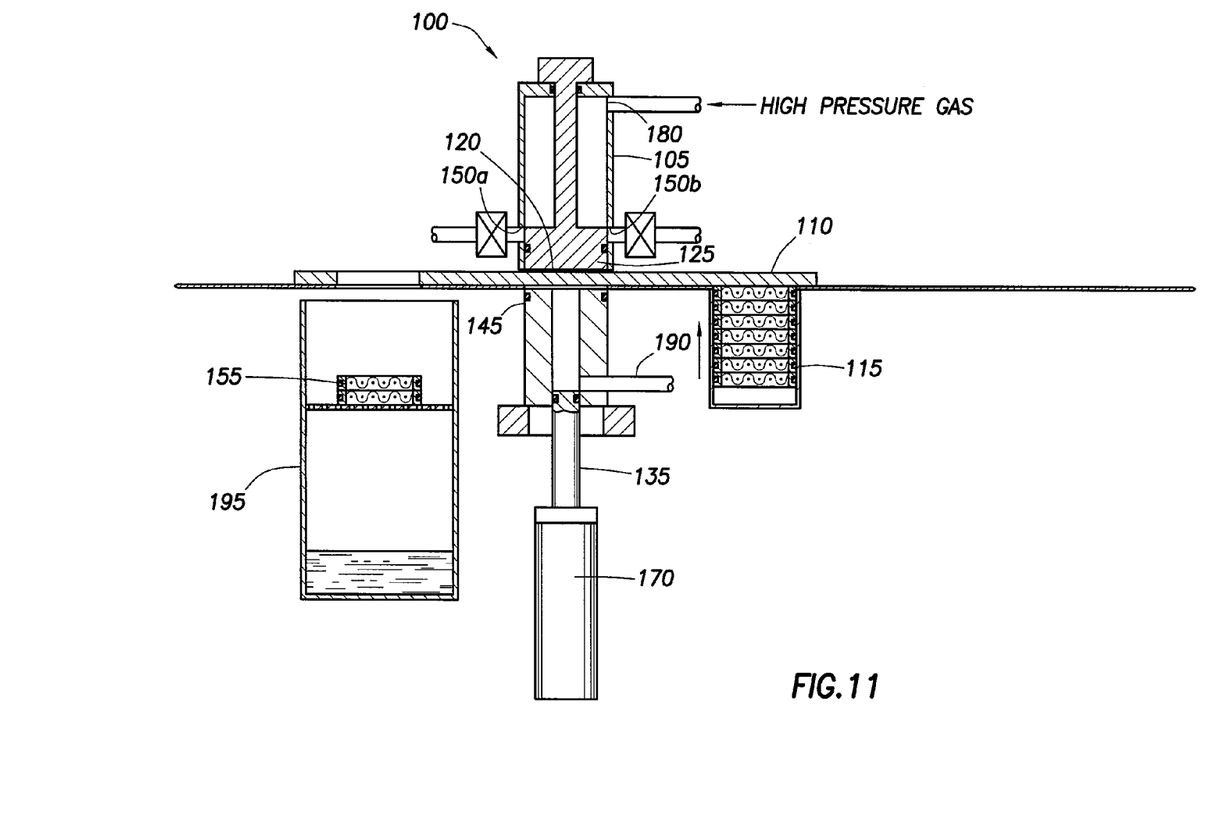
FIG. 11 illustrates a cross-sectional view of the fluid testing apparatus of FIGS. 1-10, showing the filter in a disposal area.

Referring now to FIG. 11, filter transfer mechanism 110 may move filter 155 out of testing chamber 105 and toward a disposal area 195. Filter 155 may then be deposited in disposal area 195 by any suitable method. For example, disposal area 195 may be a waste basket, into which filter 155 may be dropped.

Figure 12:
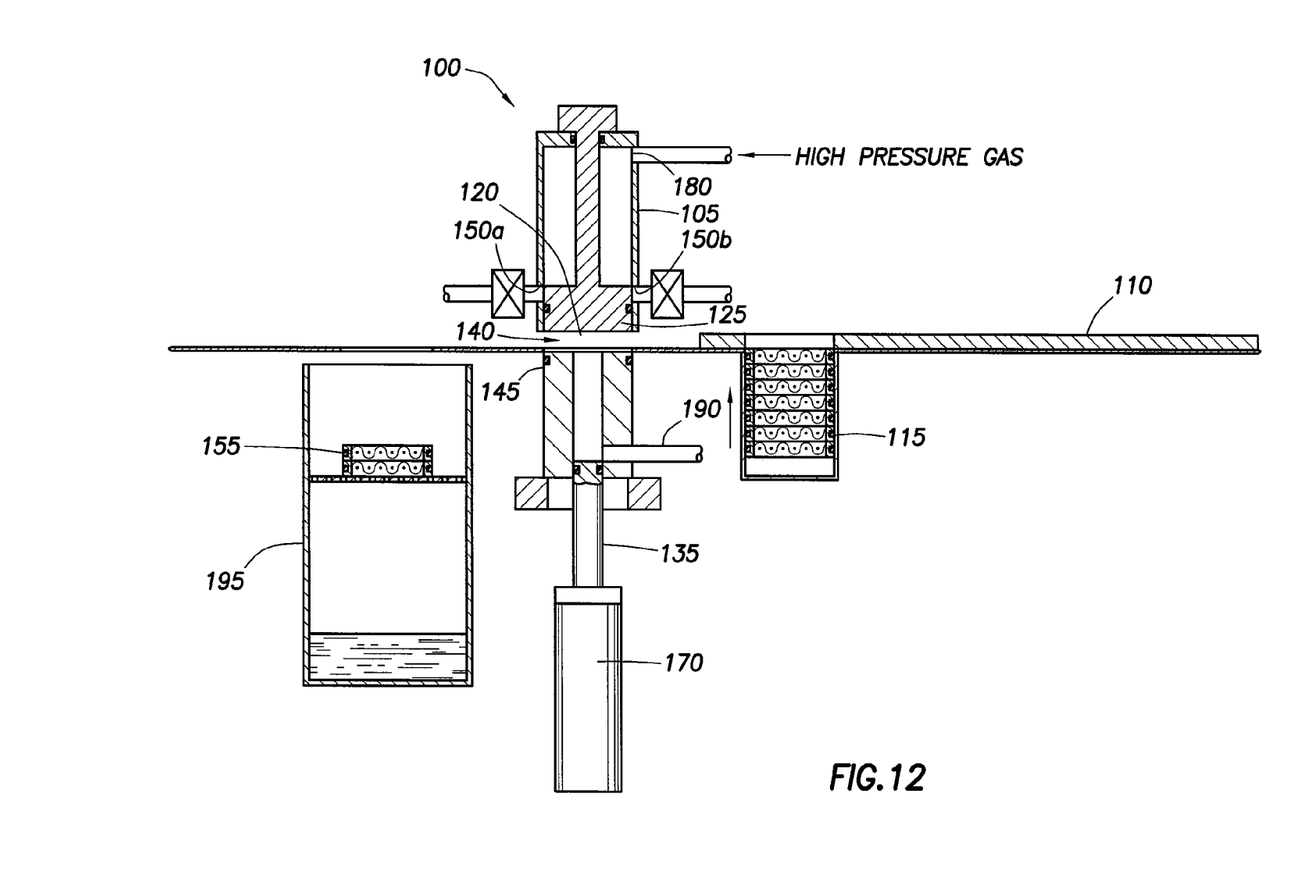
FIG. 12 illustrates a cross-sectional view of the fluid testing apparatus of FIGS. 1-11, showing the apparatus "reset" for subsequent testing.

FIG. 12 illustrates filter transfer mechanism 110 "reset" into the position shown in FIG. 1, such that subsequent testing of fluid samples may be performed, using the next filter in filter storage device 115. This may allow for a new sample to be tested immediately, without the requirement that testing chamber 105 be disassembled for cleaning and/or introduction of a new sample. This may result in a much faster cycle time.

A housing (not shown) may be provided to surround the instrument from corrosive and flammable gas environments. Filter storage device 115 and disposal area 195 may be accessed periodically via an airlock, or the entire instrument housing can be equipped with a purge system to permit periodic servicing to add new and remove spent filters."

Although not depicted in these embodiments, one of ordinary skill in the art, with the benefit of this disclosure, will recognize that fluid testing apparatus 100 may include hydraulics, pneumatics, and electropneumatics to allow for pressurization, heating, cooling, and control of fluid testing, introduction, and removal. In certain embodiment, fluid testing apparatus 100 may be controlled solely with a computer processor (not shown), thereby eliminating the need for a human operator. Additionally, separate sensors may be added in any of a number of locations to make specific measurements. For example, thermocouples and pressure transducers may verify the fluid conditions under which data are collected. Likewise, more sophisticated sensors may be incorporated to measure such things as dielectric constant, density and viscosity of the sample and filtrate in real time during the test protocol in order to provide an enhanced picture of the drilling fluid properties.

Fluid testing apparatus 100 may be used in methods for high temperature, high pressure filtration tests. One example of a method may comprise providing a fluid testing apparatus comprising a testing chamber comprising a sample volume, a filtrate collection reservoir, an opening between the sample volume and the filtrate collection reservoir, and at least one port into the sample volume; a filter storage device; and a filter transfer mechanism; positioning at least one filter in the opening using the filter transfer mechanism; closing the opening; introducing a sample fluid into the port to at least partially fill the sample volume; pressurizing the sample volume; allowing a filtrate of the sample fluid to flow from the sample volume, through the filter and into the filtrate collection reservoir; measuring the volume of filtrate passing into the filtrate collection reservoir; discharging sample fluid from the sample volume; discharging filtrate from the filtrate collection reservoir; and removing the filter. The method may further comprise cleaning the testing chamber, recording the volume of filtrate collected in real-time, and/or monitoring properties of the sample fluid. The fluid testing apparatus may further comprise a computer processor. The sample fluid may be a drilling fluid, an invert emulsion, an oil-based fluid, a water based fluid, or a fracturing fluid and the filter transfer mechanism may comprise a shuttle and/or at least one reel of continuous filter media.

Fluid testing apparatus 100 may comprise a testing chamber comprising: a sample volume and a filtrate collection reservoir, with an opening therebetween; a filtrate volume detector; and at least one port; a filter storage device; and a filter transfer mechanism. The testing chamber may further comprise a floating piston positioned within the sample volume, and the filtrate volume detector may be positioned within the filtrate collection reservoir. The testing chamber may further comprise a filtrate support. The fluid testing apparatus may further comprise a computer processor. The filter transfer mechanism may comprise a shuttle and/or at least one reel of continuous filter media.

Fluid testing apparatus 100 may alternatively be used in systems for high temperature, high pressure filtration tests. One example of a system may comprise a fluid testing apparatus comprising a testing chamber comprising a sample volume and a filtrate collection reservoir, with an opening therebetween, a filtrate volume detector, and at least one port; a filter storage device; a filter transfer mechanism; at least one filter positioned between the sample volume and the filtrate collection reservoir; and a sample fluid in the testing chamber. The testing chamber may further comprise a floating piston positioned within the sample volume, and the filtrate volume detector may be positioned within the filtrate collection reservoir. The testing chamber may further comprise a filtrate support. The system may further comprise a computer processor. The filter transfer mechanism may comprise a shuttle and/or at least one reel of continuous filter media. The sample fluid may be a drilling fluid, an invert emulsion, an oil-based fluid, a water based fluid, or a fracturing fluid.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. In particular, every range of values (of the form, "from about a to about b," or, equivalently, "from approximately a to b," or, equivalently, "from approximately a-b") disclosed herein is to be understood as referring to the power set (the set of all subsets) of the respective range of values, and set forth every range encompassed within the broader range of values. Also, the terms in the claims have their plain, ordinary meaning unless otherwise explicitly and clearly defined by the patentee.

What is claimed is:

1. A fluid testing method comprising:
   providing a fluid testing apparatus comprising:
      a testing chamber comprising
         a sample volume,
         a filtrate collection reservoir,
         an opening between the sample volume and the filtrate collection reservoir, and
         at least one port into the sample volume;
      a filter storage device; and
      a filter transfer mechanism;
   positioning at least one filter in the opening using the filter transfer mechanism;
   closing the opening;
   introducing a sample fluid into the port to at least partially fill the sample volume;
   pressurizing the sample volume;
   allowing a filtrate of the sample fluid to flow from the sample volume, through the filter and into the filtrate collection reservoir;
   measuring the volume of filtrate passing into the filtrate collection reservoir;
   discharging sample fluid from the sample volume;
   discharging filtrate from the filtrate collection reservoir; and
   removing the filter.

2. The fluid testing method of claim 1, further comprising cleaning the testing chamber.

3. The fluid testing method of claim 1, further comprising recording the volume of filtrate collected in real-time.

4. The fluid testing method of claim 1, further comprising monitoring properties of the sample fluid.

5. The fluid testing method of claim 1, wherein the fluid testing apparatus further comprises a computer processor.

6. The fluid testing method of claim 1, wherein the sample fluid is a drilling fluid, an invert emulsion, an oil-based fluid, a water based fluid, or a fracturing fluid.

7. The fluid testing method of claim 1, wherein the filter transfer mechanism comprises a shuttle.

8. The fluid testing method of claim 1, wherein the filter transfer mechanism comprises at least one reel of continuous filter media.

9. A fluid testing apparatus comprising:
   a testing chamber comprising:
      a sample volume and a filtrate collection reservoir, with an opening therebetween;
      a filtrate volume detector; and
      at least one port;
   a filter storage device; and
   a filter transfer mechanism.

10. The fluid testing apparatus of claim 9,
    wherein the testing chamber further comprises a floating piston positioned within the sample volume, and
    wherein the filtrate volume detector is positioned within the filtrate collection reservoir.

11. The fluid testing apparatus of claim 9, wherein the testing chamber further comprises a filtrate support.

12. The fluid testing apparatus of claim 9, further comprising a computer processor.

13. The fluid testing apparatus of claim 9, wherein the filter transfer mechanism comprises a shuttle.

14. The fluid testing apparatus of claim 9, wherein the filter storage device comprises at least one reel of continuous filter media.

15. A fluid testing system comprising:
    a fluid testing apparatus comprising
       a testing chamber comprising
          a sample volume and a filtrate collection reservoir, with an opening therebetween,
          a filtrate volume detector, and
          at least one port;
       a filter storage device;
       a filter transfer mechanism;
       at least one filter positioned between the sample volume and the filtrate collection reservoir; and
       a sample fluid in the testing chamber.

16. The fluid testing system of claim 15,
    wherein the testing chamber further comprises a floating piston positioned within the sample volume, and
    wherein the filtrate volume detector is positioned within the filtrate collection reservoir.

17. The fluid testing system of claim 15, wherein the testing chamber further comprises a filtrate support.

18. The fluid testing system of claim 15, further comprising a computer processor.

19. The fluid testing system of claims 15, wherein the filter transfer mechanism comprises a shuttle.

20. The fluid testing system of claim 15, wherein the sample fluid is a drilling fluid, an invert emulsion, an oil-based fluid, a water based fluid, or a fracturing fluid.

* * * * *